(12) United States Patent
Chappel

(10) Patent No.: US 6,348,444 B1
(45) Date of Patent: Feb. 19, 2002

(54) HUMAN GROWTH HORMONE TO STIMULATE HEMATOPOIESIS AND IMMUNE RECONSTITUTION AFTER HEMATOPOIETIC STEM CELL TRANSPLANTATION IN HUMANS

(75) Inventor: Scott C. Chappel, Milton, MA (US)

(73) Assignee: Applied Research Systems ARS Holding N.V., Curacao (NL)

(*) Notice: Subject to any disclaimer, the term of this patent is extended or adjusted under 35 U.S.C. 154(b) by 0 days.

(21) Appl. No.: 09/465,461

(22) Filed: Dec. 17, 1999

Related U.S. Application Data
(60) Provisional application No. 60/112,668, filed on Dec. 17, 1998.

(51) Int. Cl.$^7$ ............................................... A61K 38/27
(52) U.S. Cl. ........................... 514/2; 424/93.7; 514/12; 514/21
(58) Field of Search ........................ 424/93.7; 435/372; 514/2, 12, 21

(56) References Cited

U.S. PATENT DOCUMENTS 5,199,942 A    4/1993  Gillis

FOREIGN PATENT DOCUMENTS

WO    9428916    12/1994

OTHER PUBLICATIONS

Migashita, Y. Nippon Naibunpi Gakkai Zasshi. 67(7):785–95. Jul. 20, 1991 Abstract Only.
Patent Abstracts of Japan, Pub. No. 07101877, Pub. Date Apr. 18, 1995 Abstract Only.
Becker et al., "Chamical, Physical and Biological Characterization of a Dimeric Form of Biosynthetic Human Growth Hormone", *Biotechnology and Applied Biochemistry*, vol. 9, pp.4780487, (1987).
Becker et al., "Isolation and Characterization of a Sulfoxide and a Desamido Derivative of Biosynthetic Human Growth Hormone", *Biotechnology and Applied Biochemistry*, vol. 10, pp. 326–337, (1988).
Bewley et al., "The Chemistry of Human Pituitary Growth Hormone", *Adv. Enzymol. Relat. Area. Mol. Biol* vol. 42, pp. 73–166, (1975).
Broyer et al., "Result and side–effect of treating children with growth hormone after kidney transplantation –a preliminary report", *Acta Paediatr. Suppl.*, vol. 417, pp. 76–79, (1996).
Wikland et al., "Daily Subcutaneous Administration of Human Growth Hormone in Growth Hormone Deficient Children", *Acta Paediatr. Scand.*, vol. 75, pp. 89–97, (1986).
Appelbaum, "The Use of Colony Stimulating Factors in Marrow Transplantation", *Cancer*, vol. 72, pp. 3387–3392 (1993).

Adelman et al., "In vitro Deletional Mutagenesis for Bacterial Production of the 20,000–Dalton form of Human Pituitary Growth Hormone", *DNA*, vol. 2, No. 3, (1983).
Cunningham et al., "Dimerization of Human Growth Hormone by Zinc", *Science*, vol. 253, pp. 545–548, (1991).
Fischer et al., "Stem cell transplantation for immunodeficiency", *Springer Semin Immunopathol*, vol. 19 pp. 479–492, (1998).
Denoto et al., "Human growth hormone DNA sequence and mRNA Structure: possible alternative splicing" *Nucleic Acids Research*, vol. 9, No. 15, pp. 3719–3730, (1981).
Fine et al., "Recombinant human growth hormone treatment of children following renal transplantation", *Pediatr. Nephrol.*, vol. 5, pp. 147–151, (1991).
Friedman, "Growth hormone is not safe for children with renal transplants", *J. Pediatr.*, vol. 131, pp. S25–.*
Geffner, "Effects of growth hormone and insulin–like growth factor I on T–0 and –B–lymphocytes and immune function", *Acta Paediatr. Suppl.*, vol. 423, pp. 76–79, (1997).*
Gertler et al., "Inhibition of Lactogenic Activities of Ovine Prolactin and Human Growth Hormone (hGH) by a Novel Form of a Modified Recombinant hGH", *Endocrinology*, vol. 118, No. 2, (1986).*
Goeddel et al., "Direct expression in *Escherichia coli* of a DNA sequence coding for human growth hormone" *Nature*, vol. 281, pp. 544–548, (1979).*
Hendricks et al., "Plasma Clearence of Intravenously Administered Pituitary Human Growth Hormone: Gel Filtration Studies of Heterogeneous Components", *J. Clin. Endo. Meta.*, vol. 60, No. 5, pp. 864–867, (1985).*
Johansson et al., "Recombinant Human Growth Hormone Treatment in Short Children with Chronic Renal Disease before Transplantation or with Functioning Renal Transplants: an Interim Report on Five European Studies" *Acta Paediatr Scand*, vol. 370, pp. 36–42, (1990).*
Jorgensen et al., "Serum profiles and short–term metabolic effect of pituitary and authentic biosynthetic human growth hormone in man", *Acta Endocrinologica*, vol. 116, pp. 381–386, (1987).*
Jergenson et al., "Pharmacokinetics of Biosynthetic and Pituitary Human Growth Hormones in Rats", *Pharmacology & Toxicology*, vol. 63, pp. 129–134, (1988).*
Kimata et al., "Effects of Growth Hormone and Insulin–Like Growth Factor–I on Immunoglobulin Production by and Growth of Human B Cells", *J. Clin. Endo. Met.*, vol. 78, No. 3, (1994).*
Lewis et al., "An Interchain Disulfide Dimmer of Human Growth Hormone", *The Journal of Biological Chemistry* vol. 252, No. 11, pp. 3697–3702, (1977).*

(List continued on next page.)

Primary Examiner—David Saunders
(74) Attorney, Agent, or Firm—Browdy and Neimark

(57) ABSTRACT

The invention relates to the use of human growth hormone for the manufacture of a medicament for stimulating hematopoiesis and immune reconstitution to be administered to a patient in need thereof about 30 days post–transplantation of hematopoietic stem cells.

18 Claims, No Drawings

OTHER PUBLICATIONS

Lewis et al., "Enhancement of the Hyperglycemic Activity of Human Growth Hormone by Enzymic Modification" *ENDO.*, vol. 101, No. 5, pp. 1587–1603, (1977).*

Lewis et al., "Human Growth Hormone: Additional Members of the Complex", *ENDO.*, vol. 104, No. 5, pp. 1256–1265 (1979).*

Lewis et al., "Altered Proteolytic Cleavage of Human Growth Hormone as a Result of Deamidation", *J. Biolog. Chem.*, vol. 256, No. 22, pp. 11645–11650, (1981).*

Merchav et al., Enhancement of erythropoiesis in vitro by human growth hormone is mediated by insulin–like growth factor I, *Br. J. Haematol.*, vol. 70, pp. 267–271, (1988).*

Miller et al., "Erythropoietin After Bone Marrow Transplantation", *Hematol. Oncol. Clin. North Am.*, vol. 8 pp. 975–992, (1994).*

Moore et al., "Equivalent Potency and Pharmacokinetics of Recombinant Human Growth Hormones with or without an N–Terminal Methionine", *ENDO.*, vol. 122, No. 6, pp. 2920–2926, (1988).*

Sarna et al., "Recombinant Human Growth Hormone Improves Growth in Children Receiving Glucocorticid Treatment after Liver Transplantation", *J. Clin. Endo. Meta.*, vol. 81, No. 4, (1996).

Singh et al., "Modified Forms of Human Growth Hormone with Increased Biological Activities", *ENDO.*, vol. 94 No. 3, (1974).

Stolar et al., "Plasma "Big" and "Big–Big" Growth Hormone (GH) in Man: An Oligomeric Series Composed of Structurally Diverse GH Monomers", *J. Clin. Endo. Meta.*, vol. 59, No. 2, (1984).

Stolar et al., "Big Growth Hormone Forms in human Plasma: Immunochemical Evidence for Their Pituitary Origin", *Metabolism*, vol. 35, No. 1, pp. 75–77, (1986).

Ussing, "Zinc in the Anterior Pituitary of Rat: A Histochemical and Analytical Works", *Neuroendocrinology* vol. 45, pp. 233–242, (1987).

Tian et al., "Recombinant Human Growth Hormone Promotes Hematopoietic Reconstruction after Syngeneic Bone Marrow Transplantation in Mice", *Stem Cells*, vol. 16, pp. 193–199, (1998).

Valerio et al., "Assessment of Red Blood Cell Indices in Growth–Hormone–Treated Children", *Horm.Res.* vol. 47, pp. 62–66, (1997).

Vihervuori et al., "Hemoglobin Level is Linked to Growth Hormone–Dependent Proteins in Short Children" *Blood*, vol. 87, No. 5, pp. 2075–2081, (1996).

Waters et al., "Economics analyses of bone marrow and blood stem cell transplantation for leukemias and lymphoma: what do we Know:", *Bone Marrow Transplants*, vol. 21, pp. 641–650, (1998).

Wiedermann et al., "In vivo Activation of Circulating Monocytes by Exogenous Growth Hormone in Man", *Brain Behav. Immun.*, vol. 6, pp. 387–393, (1992).

Van Hoef et al., "Haematological recovery after high–dose consolif=dation chemotherapy with peripheral blood progenitor cell rescue: the effects of the mobilization regimen and post–transplant growth factors" *Netherlands Journal of Medicine*, vol. 52, pp. 30–39, (1998).

Anderlini et al., "The Use of Mobilized Peripheral Blood Stem Cells from Normal Donors for Allografting" *Stem Cells*, vol. 15, pp. 9–17, (1997).

Murphy et al., "Growth Hormone Exerts Hematopoietic Growth–Promoting Effects In Vivo and Partially Counteracts the Myelosuppressive Effects of Azidothymidine", *Blood*, vol. 80, No. 6, pp. 1443–1447, (1992).

Murphy et al., "Human growth hormone promotes engraftment of murine or human T cells in severe combined immunodeficient mice", *Proc. Natl. Acad. Sci.*, vol. 89, pp. 4481–4485, (1992).

Korbling et al., "Allogeneic peripheral blood stem cell transplantation using normal patient–related pediatric donors", *Bone Marrow Transplantation*, vol. 18, pp. 885–890, (1996).

Ohmizono et al., "Thrombopoietin augments ex vivo expansion of human cord blood–derived hematopoietic progenitors in combination with stem cell factor and flt3 ligand", vol. 11, pp. 524–530, (1997).

* cited by examiner

HUMAN GROWTH HORMONE TO STIMULATE HEMATOPOIESIS AND IMMUNE RECONSTITUTION AFTER HEMATOPOIETIC STEM CELL TRANSPLANTATION IN HUMANS

CROSS-REFERENCE TO RELATED APPLICATIONS

The present application claims the benefit of priority under 35 U.S.C. §119(e) from U.S. provisional application No. 60/112,668, filed Dec. 17, 1998.

BACKGROUND OF THE INVENTION

1. Field of Invention

The invention relates to the use of human growth hormone for the manufacture of a medicament for stimulating hematopoiesis and immune reconstitution in human patients following hematopoietic stem cell transplantation.

2. Description of the Related Art

Human growth hormone (hGH), also known as somatotropin, is a protein hormone produced and secreted by the somatotropic cells of the anterior pituitary. Human growth hormone plays a key role in somatic growth through its effects on the metabolism of proteins, carbohydrates and lipids. In addition to its effects on somatic growth, hGH has been shown to stimulate hematopoiesis (proliferation, maturation and function of erythroid, mycloid and lymphoid lineages).

The erythropoietic stimulatory effect of hGH treatment, both in healthy and in growth hormone deficient (GHD) patients has been reported in scientific publications. For instance, Valerio et al (1997) reported that, in vivo, erythropoiesis markers, such as hemoglobin (Hb), hematocrit (Ht) and red blood cell (RBC) counts, increased in GHD children following hGH therapy. Furthermore, it has been reported that increases in Hb in response to hGH treatment were similar in patients with hGH deficiency and those with normal hGH secretion (Vihervuori et al, 1996).

Moreover, recent publications show that hGH increases the proliferation and the maturation/function of the myeloid cell series. Human growth hormone enhances myeloid colony formation (Merchav et al, 1988), primes granulocyte oxidative metabolic burst in healthy and uremic children (Derfalvi et al, 1998) and enhances monocyte chemotaxis (Wiedermann et al, 1992).

Finally, several reports demonstrate that hGH exerts stimulatory effects on proliferation and maturation of the lymphoid cell series. Derfalvi et al (1998) describes that hGH administration stimulates the lymphoproliferation in healthy and uremic children, and Kimata et al (1994) determined that hGH enhances both proliferation and Ig production in plasma cell lines. Geffner (1997) mentioned that hGH has been shown to stimulate CD8+ cell counts and, to a lesser extent, CD4+ cell counts.

Bone marrow transplantation and circulating blood stem cell transplantation (hereafter both referred as hematopoietic stem cell transplantation (HSCT)) are the treatment of choice in several disorders, including malignancies, Severe Combined Immune Deficiencies (SCID), congenitally or genetically determined hematopoietic abnormalities, anemia, aplastic anemia, leukemia and osteoporosis (Fischer et al, 1998). During the past ten years, the use of HSCT grew from less than 5,000 to more than 40,000 annually (Waters et al, 1998).

Autologous HSCT defines a stem cell transplantation in which donor and recipient are the same individual. Non-autologous HSCT comprises HSCT in which donor and recipient are different individuals, either genetically identical (syngenic) or genetically different (allogenic).

Non-autologous HSCT is subject to immunological reactions, i.e., graft-versus-host disease and host-versus-graft reaction (graft rejection). The mechanisms of graft rejections are not completely known, but in addition to immune mechanisms, hematopoietic stem cells may also be rejected by natural killer (NK) cells. The recipient's immune system must be ablated to permit successful non-autologous HSCT.

To prepare for HSCT, the recipient's immune system is destroyed with radiation and/or chemotherapy. This procedure not only prevents non-autologous graft rejection but also serves to kill leukemic cells if that is the patient's disease. Following HSCT, hematopoietic and immune cells of the recipients are replaced with those from the donor.

Effective treatments aimed at accelerating hematopoiesis and immune reconstitution are of great interest not only to promote engraftment but also to reduce the risk of infections and to shorten the time of hospitalization. Granulocyte-macrophage colony stimulating factor (GM-CSF) and granulocyte colony stimulating factor (G-CSF) have been shown to accelerate marrow recovery and to increase engraftment through stimulation of stem cell proliferation (Appelbaum, 1993). Similarly, recombinant human erythropoietin (rhEPO) has been shown to enhance erythroid engraftment after allogenic bone marrow transplantation and to decrease transfusion requirements (Miller et al, 1994). These growth factor treatments have demonstrated promising results in clinical trials and are currently used to improve the outcome of HSCT.

In that respect, human growth hormone represents an attractive alternative therapy since it exerts a stimulatory effect on the three hematopoietic progenitor cell series.

In rodents, it was reported that, after syngenic bone marrow transplantation in mice, hGH-treated animals exhibit significant increases in total hematopoietic progenitor cell content in both bone marrow and spleen (Tian et al, 1998). Tian et al further specified an increase in erythropoietic marker (Hb, Ht, RBC), in erythroid cell progenitor content, in granulocyte marker 8C5+ and, finally, in RBC and platelet recovery after bone marrow transplantation (BMT); and demonstrated the benefit of hGH therapy to stimulate immune reconstitution after BMT in mice. Furthermore, Tian et al suggested that hGH may be of clinical use for accelerating hematopoiesis after autologous bone marrow transplantation. The sudies leading to these results were carried out in mice. Doses of rhGH were administered to irradiated and transplanted mice after syngeneic bone marrow transplantation. The mice received the same dose of rhGH from day one every second day to a maximum of 20 days. Tian et al reported, that the hematopoietic growth-promoting effects of rhGH after SBMT did not result in toxicity or weight gain.

However, when administered to humans, human growth homone was also shown to have some drawbacks.

Human growth hormone was shown to increase the incidence of graft rejection, for instance. In growth-retarded, kidney-transplanted children, rejection episodes are more frequent in hGH treated patients than in the placebo group (Fine et al, 1991). Friedman (1997) reported that recombinant hGH treatment is not safe for children with renal transplants. Friedman argued that the hGH-mediated up-regulation of immune function could be a reason for the increased loss of renal function caused by rejection and pointed out that hGH should not be administered to children after renal allograft. In a large clinical trial assessing the results and side effects of treating children with hGH after kidney transplantation, hGH treatment was been correlated with an increased frequency of acute graft rejection, particularly in those patients who had a history of more than one episode (Johansson et al, 1990; Broyer, 1996). Finally, in liver transplantation, hGH improves growth in children receiving glucocorticoid treatment but also increases the risk of allogenic graft rejection (Sarna et al, 1996).

In the light of the data presented above, hGH therapy following HSCT carries both profitable and deleterious effects. Human growth hormone would be beneficial through its positive effect on immune reconstitution; hGH promotes proliferation of hematopoietic progenitor cells, i.e., donor stem cells, and, thus, should facilitate engraftment. Human growth hormone treatment would also provide better protection against pathogens through overall stimulation of the immune functions. However, hGH was also shown to increase the incidence of graft rejection, which is a serious drawback of its use in treating patients.

SUMMARY OF THE INVENTION

It is therefore the object of the present invention to provide a treatment for hematopoietic stem cell transplanted patients using recombinant human growth hormone to stimulate hematopoiesis and immune reconstitution, while avoiding the deleterious side effects of hGH administration, as, for example, those outlined above.

According to the present invention, human growth hormone is used for the manufacture of a medicament for stimulating hematopoiesis and immune reconstitution in human patients to be administered to humans at about 30 days post-transplantation procedure. This innovative regimen of hGH administration is intended to circumvent the graft rejection induced by hGH.

DEFINITIONS

In order to provide a clearer and more consistent understanding of the specification and claims, including the scope to be given to such terms, the following definitions are provided.

Hematopoietic stem cell transplantation (HSCT): A clinical procedure in which pluripotent hematopoietic stem cells obtained from bone marrow or circulating blood are transplanted to a patient.

Bone marrow transplantation (BMT): A clinical procedure in which pluripotent hematopoietic stem cells obtained from bone marrow are transplanted to a patient.

Autologous transplantation: Transplantation in which the donor and the recipient are the same individual.

Non-autologous transplantation: Transplantation in which the donor and the recipient are different individuals from the same species, either genetically identical (syngenic transplantation) or genetically different (allogenic transplantation).

DETAILED DESCRIPTION OF THE INVENTION

The laboratory of the present inventor has surprisingly discovered that, if human growth hormone is administered to patients at about 30 days post-transplantation, the beneficial effects of human growth hormone, i.e., stimulation of hematopoiesis and immune function are maintained, while deleterious side effects, i.e., increased risk of graft rejection, are reduced if not eliminated.

Therefore, the invention relates to the use of human growth hormone for the manufacture of a medicament for stimulating hematopoiesis and immune reconstitution in human patients to be administered about 30 days post-transplantation of hematopoietic stem cells.

The medicament used according to the invention comprises an effective amount of hGH. The effective amount of human growth hormone preferably comprises about 0.01 to 0.50 mg per kg per week. More preferably, it comprises about 0.10 to 0.30 mg per kg per week.

In a highly preferred embodiment of the invention, the effective amount of human growth hormone comprises about 0.20 mg per kg per week. This means, that for an average adult individual of 70 kg of weight, a weekly amount of 14 mg of human growth hormone is administered. The human growth hormone is preferably administered in single doses of about 0.07 mg/kg every other day.

Human growth hormone may be administered for an extended period of time, like for several months or even years.

In preferred embodiments, the medicament is administered systemically. Advantageously, it may be administered subcutaneously or intramuscularly.

Preferably, the medicament further comprise a pharmaceutically acceptable carrier, excipient, stabilizer or auxiliary agent. A preferred formulation of a pharmaceutical composition containing human growth hormone is described in WO9535116, this being a composition stabilized by means of saccharose. The medicament according to the invention may be stored as a lyophilisate of human growth hormone.

In a preferred embodiment of the invention, the medicament comprising human growth hormone is not administered before 30 days post-transplantation.

Human growth hormone (hGH), also known as somatotropin, is a protein hormone produced and secreted by the somatotropic cells of the anterior pituitary. HGH plays a key role in somatic growth through its effects on the metabolism of proteins, carbohydrates and lipids.

Human growth hormone is a single polypeptide chain of 191 amino acids (SEQ ID NO:1; Bewley et al., 1975) having two disulfide bonds, one between Cys-53 and Cys-165, forming a large loop in the molecule, and the other between Cys-182 and Cys-189, forming a small loop near the C-terminus.

Several alternative forms of hGH are known, including naturally-occurring derivatives, variants and metabolic products, degradation products primarily of biosynthetic hGH and engineered variants of hGH produced by genetic methods. Any form of hGH can be used for the purpose of the present invention, as long as it retains the biological activity of hGH.

Methionyl hGH was the first form of hGH to be produced through recombinant DNA technology. This compound is actually a variant of hGH having one additional methionine residue at its N-terminus (Goeddel et al, 1979).

The use according to the invention therefore also comprises a medicament comprising a variant of the human growth hormone, this variant being preferably methionyl hGH, having one additional methionine residue at its N-terminus.

A naturally-occurring variant of hGH called 20-K-hGH has been reported to occur in the pituitary, as well as in the bloodstream (Lewis et al, 1978; Lewis et al, 1980). This compound, which lacks the 15 amino acid residues from Glu-32 to Gln-46, arises from an alternative splicing of the messenger ribonucleic acid (DeNoto et al, 1981). This compound shares many, but not all, of the biological properties of hGH.

The use according to the invention therefore also comprises a medicament comprising a hGH-variant which lacks the 15 amino acid residues from Glu-32 to Gln-46.

HGH that is acetylated at the N-terminus has been isolated and identified (Lewis et al, 1979). It is not clear if acetylation serves as a regulatory role or is simply an artifact of the purification.

The use according to the invention further comprises a medicament comprising hGH which is acetylated at the N-terminus.

Human growth hormone is a mixture of monomer, dimer and higher molecular weight oligomers. Additionally, there are aggregated forms of human growth hormone found both in the pituitary and in the circulation (Stolar et al, 1984; Stolar et al, 1986). There appears to be three distinct types of dimer: a disulfide dimer connected through interchain disulfide bonds (Lewis et al, 1977); a covalent or irreversible dimer that is detected on sodium dodecylsulfate-polyacrylamide gels and is not a disulfide dimer (Bewley et al, 1975); and a non-covalent dimer which is easily dissociated into monomeric hGH by treatment with agents that disrupt hydrophobic interactions in proteins (Becker et al, 1987). In addition, human growth hormone forms a dimeric complex with $Zn^{2+}$ (Cunningham et al, 1991). Scatchard analysis has revealed that two $Zn^{2+}$ ions associate per hGH dimer in a cooperative fashion, and this $Zn^{2+}$-hGH dimeric complex was found to be more stable to denaturation than monomeric hGH (Cunningham et al, 1991).

The use according to the invention also comprises a medicament comprising a dimer of human growth hormone selected from the group consisting of a disulfide dimer connected through interchain disulfide bonds, a covalent irreversible non-disulfide dimer, a non-covalent dimer, and mixtures thereof.

A number of derivatives of hGH arise from proteolytic modifications of the molecule. The primary pathway for the metabolism of hGH involves proteolysis, and several derivatives of hGH having nicks or deletions in this region have been described (Thorlacius-Ussing, 1987). This region is in the large loop of hGH, and cleavage of a peptide bond there results in the generation of two chains that are connected through the disulfide bond at Cys-53 and Cys-165. Many of these two-chain forms are reported to have increased biological activity (Singh et al, 1974). Many derivatives of human growth hormone have been generated artificially through the use of enzymes. The enzymes trypsin and subtilisin, as well as others, have been used to modify hGH at various points throughout the molecule (Lewis et al, 1977). One such derivative, called two-chain anabolic protein (2-CAP), was formed through the controlled proteolysis of hGH using trypsin. 2-CAP was found to have biological properties very distinct from those of the intact hGH molecule, in that the growth-promoting activity of hGH was largely retained, and most of the effects on carbohydrate metabolism were abolished.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, 1981). Deamidated hGH has been shown to have an altered susceptibility to proteolysis with the enzyme subtilisin, suggesting that deamidation may have physiological significance in directed proteolytic cleavage of hGH. Biosynthetic hGH is known to degrade under certain storage conditions, resulting in deamidation at a different asparagine (Asn-149). This is the primary site of deamidation, but deamidation at Asn-152 is also seen (Becker et al, 1988). Deamidation at Gln-137 has not been reported in biosynthetic hGH.

The use according to the invention therefore also comprises a medicament, wherein the human growth hormone is deaminnated.

Methionine residues in proteins are susceptible to oxidation, primarily to the sulfoxide. Both pituitary-derived and biosynthetic hGH undergo sulfoxidations at Met-14 and Met-125 (Becker et al, 1988). Oxidation at Met-170 has also been reported in pituitary but not biosynthetic hGH. Both desamide hGH and Met-14 sulfoxide hGH have been found to exhibit full biological activity (Becker et al, 1988).

The use according to the invention therefore also comprises a medicament, wherein the human growth hormone is sulfoxidized at one or more methionine residues.

Truncated forms of hGH have been produced, either through the actions of enzymes or by genetic methods. 2-CAP, generated by the controlled actions of trypsin, has the first eight residues at the N-terminus of hGH removed. Other truncated versions of hGH have been produced by modifying the gene prior to expression in a suitable host. The first 13 residues have been removed to yield a derivative having distinctive biological properties in which the polypeptide chain is not cleaved (Gerler et al, 1986).

Although human growth hormone was originally obtained from pituitary glands of cadavers, these preparations were not electrophoretically homogeneous, and antibodies appeared in the serum of patients treated with preparations on the order of 50% purity, the immunogenicity being attributed to inactive components. Recombinant DNA technology permitted production of an unlimited supply of hGH in a number of different systems. Purification of hGH from the culture medium is facilitated by low amounts of contaminating proteins present. In fact, it has been shown that hGH can be purified on a laboratory scale by a single purification step on a reversed-phase HPLC column.

In a preferred embodiment of the present invention, recombinantly produced human growth hormone is used.

Recombinant hGH is generally marketed as vials containing hGH plus additional excipients, e.g., glycine and mannitol, in a lyophilized form. A companion diluent vial is provided, allowing the patient to reconstitute the product to the desired concentration prior to administration of the dose. The amounts of hGH per vial may be 4 to 6 mg, for example.

After intravenous administration, the elimination of hGH is described by first-order kinetics with a serum half-life of 12–30 minutes in both animals and humans (Moore et al, 1988; Hendricks et al, 1985). Traditionally, intramuscular injection has been the method of choice as the preferred route of delivery. In humans, absorption of exogenous hGH appears to be more rapid from the intramuscular site, with a time to maximum concentration of two to three hours, compared to four to six hours after subcutaneous administration. The disappearance phase from serum has been reported to range from 12–20 hours for intramuscular administration, and 20–24 hours after subcutaneous administration (Albertsson-Wikland et al, 1986; Jorgensen et al, 1987). In general, no significant differences have been observed in the pharmacokinetics or biological activities of recombinant natural sequence hGH, recombinant N-methionyl-hGH, or pituitary-derived material in humans (Moore et al, 1988; Jorgensen et al, 1988).

The human growth hormone, as used in the present invention, can include functional derivatives as noted above, as well as other types of derivatives, fragments, variants, analogs, or chemical derivatives. A functional derivative retains at least a portion of the amino acid sequence of hGH which permits its utility in accordance with the present invention, namely treatment of HSCT.

A "fragment" of the human growth hormone, according to the present invention, refers to any subset of the molecule, that is, a shorter peptide.

A "variant" of the human growth hormone, according to the present invention, refers to a molecule which is substantially similar to either the entire peptide or a fragment thereof. Variant peptides may be conveniently prepared by direct chemical synthesis of the variant peptide, using methods well known in the art.

Alternatively, amino acid variants of hGH can be prepared by mutations in the cDNA encoding the synthesized hGH derivatives. Such variants comprise deletions, insertions or substitutions of residues within the amino acid sequence. While any combination of deletions, insertions and substitutions may also be made, provided that the final construct possesses the desired activity, it is preferred that substitutions be in a range of one to ten amino acid substitutions, more preferably one to five amino acid substitutions. It will be appreciated by those in the art that deletions and insertions, which can be readily generated at the N- or C-terminus, are well within the skill of the art to generate and test for hGH activity without undue experimentation.

At the genetic level, these variants ordinarily are prepared by site-directed mutagenesis, as exemplified by Adelman et al (1983), of nucleotides in the DNA encoding the peptide molecule, thereby producing DNA encoding the variant, and thereafter expressing the DNA in recombinant cell culture. The variants typically exhibit the same qualitative biological activity as the non-variant peptide.

An "analog" of human growth hormone, according to the present invention, refers to a non-natural molecule which is substantially similar to either the entire molecule or to an active fragment thereof.

A "chemical derivative" of human growth hormone, according to the present invention, contains additional chemical moieties not normally part of the human growth derivative amino acid sequence. Covalent modifications of the amino acid sequence are included within the scope of this invention. Such modifications may be introduced into the human growth hormone by reacting targeted amino acid residues of the peptide with an organic derivatizing agent that is capable of reacting with selected side chains or terminal residues.

The types of substitutions, which may be made in the human growth hormone according to the present invention, may be based on analysis of the frequencies of amino acid changes between a homologous protein of different species. Based upon such analysis, conservative substitutions may be defined herein as exchanges within one of the following five groups:

I. Small, aliphatic, non-polar or slightly polar residues:
   Ala, Ser, Thr, Pro, Gly
II. Polar, negatively-charged residues and their amides:
   Asp, Asn, Glu, Gin
III. Polar, positively-charged residues:
   His, Arg, Lys
IV. Large, aliphatic non-polar residues:
   Met, Leu, lie, Val, Cys
V. Large aromatic residues:
   Phe, Try, Trp Within the foregoing groups, the following substitutions are considered to be "highly conservative":
Asp/Glu
His/Arg/Lys
Phe/Tyr/Trp
Metleu/Ile/Val Semi-conservative substitutions are defined to be exchanges between two of groups I–IV above which are limited to supergroup (A), comprising I, II and III above, or to supergroup (B), comprising IV and V above. Substitutions are not limited to the genetically encoded or even the naturally-occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide is also useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters, such as methyl picolinimidate; pyridoxal phosphate; pyridoxal; chloroborohydride; trinitrobenzenesuflonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and $\epsilon$-nitro derivatives, respectively.

Carboxyl side groups (aspartyl or glutamyl) are selectively modified by reaction with carbodiimides (R'N—C—N—R'), such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

In further advantagous embodiments or the invention, the medicament used according to the invention comprises a fragment of human growth hormone. The fragment may be a truncated human growth hormone lacking the first eight amino acids or the first 13 amino acids.

The present invention is intended to treat patients undergoing non-autologous hematopoietic stem cell transplantation as a preferred embodiment of the present invention. The human growth hormone administered is preferably recombinant human growth hormone (rhGH).

While the present invention may be carried out with recombinant human growth hormone derivatives made by recombinant DNA technology, for instance, in procaryotic or eucaryotic cells, these derivatives can also be made by conventional protein synthesis methods which are well known to those skilled in the art.

The use of a medicament for administration according to the present invention can include at least hGH and/or hGH fragments, variants, analogs or chemical derivatives in a pharmaceutically acceptable form, optionally combined with an acceptable carrier.

These compositions can be administered by any means that achieve their intended purpose. For example, administration can be by parenteral, such as subcutaneous, intravenous, intramuscular, intraperitoneal, transdermal or buccal routes. The dosage administered depends upon the age, health and weight of the recipient, type of previous or concurrent treatment, if any, frequency of the treatment and the nature of the effect desired.

Suitable formulations for parenteral administration include aqueous solutions of the active compounds in water-soluble form, for example, water-soluble salts. In addition, suspension of the active compounds as appropriate oily injection suspensions may be administered.

Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Determination of amounts of hGH to be administered may also be determined individually. It is within the skill of the art. A dosage may start at about 1 microgram per kilogram patient weight per day and will be escalated until the desired effect is reached. It is understood that the suitable dose will also depend upon the age, sex and health of the recipient. The most preferred dosage will be tailored to the individual subject, as is understood and determinable by one skilled in the relevant arts. See, e.g. *Avery's Drug Treatment: Principles and Practices of Clinical Pharmacology and Therapeutics,* 3rd. Ed., ADIS Press, LTD, Williams and Wilkins, Baltimore, Md. (1987), and Ebadi, *Pharmacology,* Little, Brown and Co., Boston, Mass. (1985), which references are entirely incorporated herein by reference.

The total dose required for each treatment may be administered in multiple doses or a single dose. The composition may be administered alone or in conjunction with other therapeutics directed to the disease or directed to other symptoms thereof.

Having now fully described this invention, it will be appreciated by those skilled in the art that the same can be performed within a wide range of equivalent parameters, concentrations and conditions without departing from the spirit and scope of the invention and without undue experimentation.

While this invention has been described in conjunction with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features herein before set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

REFERENCES

Adelman et al, *DNA* 2:183–193 (1983)
Albersson-Wikland et al, *Acta Paediatr. Scand.* 75:89–97 (1986)
Appelbaum, F. R., *Cancer* 72:3387–3392 (1993)
Becker et al, *Biotechnol. Appl. Biochem.* 9:478–487 (1987)
Becker et al, *Biotechnol. Appl. Biochem.* 10:326–337 (1988)
Bewley et al, *Adv. Enzymol. Relat. Areas. Mol. Biol.* 42:73–166 (1975)
Broyer, M., *Acta Paediatr. Suppl.* 417:76–79 (1996)
Cunningham et al, *Science* 253:545–548 (1991)
DeNoto et al, *Nucleic. Acids. Res.* 9:3719–3730
Derfalvi et al, *Pediatr. Nephrol.* 5:147–151 (1991)
Fischer et al, *Spriinger Semin. Immunopathol.* 19:479–492 (1998)
Friedman, A. L., *J. Pediatr.* 131:S25–S27 (1997)
Geffner, M., *Acta Paediatr. Suppl.* 423:76–79 (1997)
Gertler et al, *Endocrinology* 118:720–726 (1986)
Goeddel et al, *Nature* 281:544–548 (1979)
Hendricks et al, *J. Clin. Endocriniol. Metab.* 60:864–867 (1985)
Johansson et al, *Acta Paediatr. Scand. Suppl.* 370:36–42 and discussion 43 (1990)
Jorgensen et al, *Acta Endocrinol. (Copenh.)* 116:381–386 (1987)
Jorgensen et al, *Pharmacol. Toxicol.* 63:129–134 (1988)
Kimata et al, *J. Clin. Endocrinol. Metab.* 78:635–641 (1994)
Lewis et al, *J. Biol. Chem.* 252:3697–3702 (1977a)
Lewis et al, *Endocrinology* 101:1587–1603 (1977b)
Lewis et al, *Endocrinology* 104:1256–1265 (1979)
Lewis et al, *J. Biol. Chem.* 256:11645–11650 (1981)
Lewis et al, *Endocrinology* 101:1587–1603 (1977b)
Merchav et al, *Br. J. Haematol.* 70:267–271 (1988)
Miller et al, *Hematol. Oncol. Clin. North Am.* 8:975–992 (1994)
Moore et al, *Endocrinology* 122:2920–2926 (1988)
Sarna et al, *J. Clin. Endocrinol. Metab.* 81:1476–1482 (1996)
Singh et al, *Endocrinology* 94:883–891 (1974)
Stolar et al, *J. Clin. Endocrinol. Meetab.* 59:212–218 (1984)
Stolar et al, *Metabolism* 35:75–77 (1986)
Thorlacius-Ussing, O., *Neuroendocrinology* 45:233–242 (1987)
Tian et al, *Stem. Cells* 16:193–199 (1998)
Valerio et al, *Horm. Res.* 47:62–66 (1997)
Vihervuori et al, *Blood* 87:2075–2081 (1996)
Waters et al, *Bone Marrow Transplant.* 21:641–650 (1998)
Wiedermann et al, *Brain Behav. Immun.* 6:387–393 (1992)

What is claimed is:

1. A method for stimulating hematopoiesis and immune reconstitution in human patients following hematopoietic stem cell transplantation, comprising the step of administering to a human patient not before about 30 days post-transplantation of hemopoietic stem cells a pharmaceutical composition comprising a pharmaceutically acceptable carrier, excipient, stabilizer or auxiliary agent, and an effective amount of the human growth hormone of SEQ ID NO:1 or a fragment, analog, variant or chemical derivative thereof, having the hematopoiesis stimulating activity of human growth hormone, as an active ingredient, with the proviso that the variant is not the 20 kDa human growth hormone variant lacking the 15 amino acid residues from Glu32 to Gln46 of SEQ ID NO:1.

2. The method according to claim 1, wherein the administered pharmaceutical composition comprises human growth hormone.

3. The method according to claim 2, wherein the human growth hormone is a recombinantly produced human growth hormone.

4. The method according to claim 1, wherein the effective amount of human growth hormone is in a range of about 0.01 to 0.50 mg per kg per week.

5. The method according to claim 4, wherein the effective amount of human growth hormone is in a range of about 0.10 to 0.30 mg per kg per week.

6. The method according to claim 5, wherein the effective amount of human growth hormone is about 0.20 mg per kg per week.

7. The method according to claim 6, wherein the human growth hormone is administered in single doses of about 0.07 mg/kg.

8. The method according to claim 1, wherein the human growth hormone is administered every other day.

9. The method according to claim 8, wherein the medicament is administered subcutaneously.

10. The method according to claim 8, wherein the medicament is administered intramuscularly.

11. The method according to claim 1, wherein the administered pharmaceutical composition comprises a variant of human growth hormone.

12. The method according to claim 11, wherein the variant human growth hormone is methionyl human growth hormone which has an additional methionine residue at the N-terminus of human growth hormone.

13. The method according to claim 1, wherein the administered pharmaceutical composition comprises a fragment of human growth hormone.

14. The method according to claim 1, wherein the administered pharmaceutical composition comprises a dimer of human growth hormone selected from the group consisting of a disulfide dimer connected through interchain disulfide bonds, a covalent irreversible non-disulfide dimer, a non-covalent dimer, and mixtures thereof.

15. The method according to claim 1, wherein the administered pharmaceutical composition comprises a chemical derivative of human growth hormone.

16. The method according to claim 15, wherein the human growth hormone is acetylated at the N-terminus.

17. The method according to claim 15, wherein the human growth hormone is deaminated.

18. The method according to claim 15, wherein human growth hormone is sulfoxidized at one or more methionine residues.

* * * * *

SEQUENCE LISTING

<160> NUMBER OF SEQ ID NOS: 1

<210> SEQ ID NO 1
<211> LENGTH: 191
<212> TYPE: PRT
<213> ORGANISM: homo sapiens

<400> SEQUENCE: 1

```
Phe Pro Thr Ile Pro Leu Ser Arg Leu Phe Asp Asn Ala Ser Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```